United States Patent
Bian et al.

(10) Patent No.: US 11,365,180 B2
(45) Date of Patent: Jun. 21, 2022

(54) RESOLUTION METHOD FOR AXIS CHIRAL ENANTIOMERS OF LESINURAD

(71) Applicant: CHINA RESOURCES SAIKE PHARMACEUTICAL CO., LTD., Beijing (CN)

(72) Inventors: Deqian Bian, Beijing (CN); Moyi Liu, Beijing (CN); Yan Yang, Beijing (CN); Fangze Chi, Beijing (CN)

(73) Assignee: CHINA RESOURCES SAIKE PHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 17/054,466

(22) PCT Filed: Apr. 26, 2019

(86) PCT No.: PCT/CN2019/084640
§ 371 (c)(1),
(2) Date: Nov. 10, 2020

(87) PCT Pub. No.: WO2019/214467
PCT Pub. Date: Nov. 14, 2019

(65) Prior Publication Data
US 2021/0053928 A1   Feb. 25, 2021

(30) Foreign Application Priority Data

May 10, 2018 (CN) .......................... 201810444393.3

(51) Int. Cl.
*C07D 249/12* (2006.01)
(52) U.S. Cl.
CPC ................................. *C07D 249/12* (2013.01)

(58) Field of Classification Search
CPC .................................................. C07D 249/12
See application file for complete search history.

(56) References Cited

FOREIGN PATENT DOCUMENTS

| CN | 101346386 A | 1/2009 |
|----|-------------|--------|
| CN | 105399694 A | 3/2016 |
| CN | 105622531 A | 6/2016 |
| CN | 107098866 A | 8/2017 |
| CN | 105985295 A | 11/2018 |

OTHER PUBLICATIONS

Wang, Jianfei et al.; Discovery and Assessment of Atropisomers of (±)-Lesinurad; ACS Med. Chem. Lett., vol. 8, No. 3, Feb. 14, 2017, ISSN: 1948-5875, pp. 299-303.

*Primary Examiner* — Shawquia Jackson
(74) *Attorney, Agent, or Firm* — Novick, Kim & Lee, PLLC; Allen Xue

(57) ABSTRACT

A resolution method of axial chiral enantiomers of lesinurad (2-(5-bromo-4-(4-cyclopropylnaphthalen-1-yl)-4H-1,2,4-triazol-3-ylthio)acetic acid) adopts inexpensive and readily available quinoline natural products and derivatives thereof, such as quinine, cinchonine, quinidine or cinconidine as resolving agents to react with lesinurad racemate in an organic solvent to form a salt, and the salt is dissociated by acidification so as to obtain optically pure (R)- or (S)-2-(5-bromo-4-(4-cyclopropylnaphthalen-1-yl)-4H-1,2,4-triazol-3-ylthio)acetic acid. The method can give axial chiral enantiomer of lesinurad in R configuration with a chiral purity ee of up to 100% and a total yield of 90% or more. The obtained axial chiral enantiomer of lesinurad in S configuration can reach a chiral purity ee of up to 99.9% and a total yield of 80% or more.

10 Claims, 5 Drawing Sheets

RESOLUTION METHOD FOR AXIS CHIRAL ENANTIOMERS OF LESINURAD

CROSS-REFERENCE TO RELATED APPLICATIONS

The application is a U.S. national entry of PCT International Application No. PCT/CN2019/084640, filed Apr. 26, 2019, which claims the priority to the earlier application No. CN201810444393.3 submitted to China National Intellectual Property Administration on May 10, 2018, which is entitled "Resolution method of axial chiral enantiomers of lesinurad". The earlier application is incorporated herein by reference in its entirety.

FIELD OF THE INVENTION

The invention belongs to the pharmaceutical field, and relates to a resolution method of axial chiral enantiomers of lesinurad (i.e. 2-(5-bromo-4-(4-cyclopropylnaphthalen-1-yl)-4H-1,2,4-triazol-3-ylthio)acetic acid).

BACKGROUND OF THE INVENTION

Lesinurad, i.e. 2-(5-bromo-4-(4-cyclopropylnaphthalen-1-yl)-4H-1,2,4-triazol-3-ylthio)acetic acid, CAS:878672-00-5, having a structure as shown in Formula 2, is an oral effective inhibitor of uric acid transporter 1 (URAT1) for the treatment of hyperuricaemia in patients with gout.

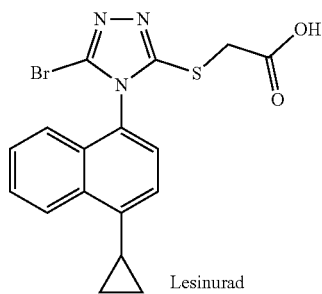

Formula 2

Lesinurad

Since lesinurad does not possess chiral atoms, it was studied as an achiral molecule in the previous research literatures. With the development of the research, it was found that due to the relatively large steric hindrance of groups located on the two sides of the triazole ring, lesinurad could not rotate freely, thus forming a chiral compound with a chiral axis similar to binaphthol.

For a compound system composed of four groups arranged in two pairs around an axis out of the plane, when each pair is different, the system may be asymmetric, which is called an axial chiral system. Binaphthols exhibit axial chirality, as shown in Formula 2-1, in which the substituents on both sides of the chiral axis are arranged in order of atomic number (A>B, A'>B'). When viewed along the axis of symmetry from one side and analyzed according to Newman projection, a pair of groups closer to the observer are ranked in the first two places in order of precedence, and the other pair of groups are ranked in the third and fourth places (no matter from which direction the molecule is viewed, the results are the same). According to the rules similar to the central chiral system, the smallest group B' is placed in the direction farthest away from the observer. If the observer observes that A→B→A' is clockwise, the axial chiral compound is defined as R configuration; on the contrary, the axial chiral compound is defined as S configuration. This kind of axial chiral compounds can also be expressed in other ways, such as M or P, where M corresponds to R and P corresponds to S. R and S enantiomers are isomers of each other, and the racemate is an equimolar mixture of R and S enantiomers.

Formula 2-1

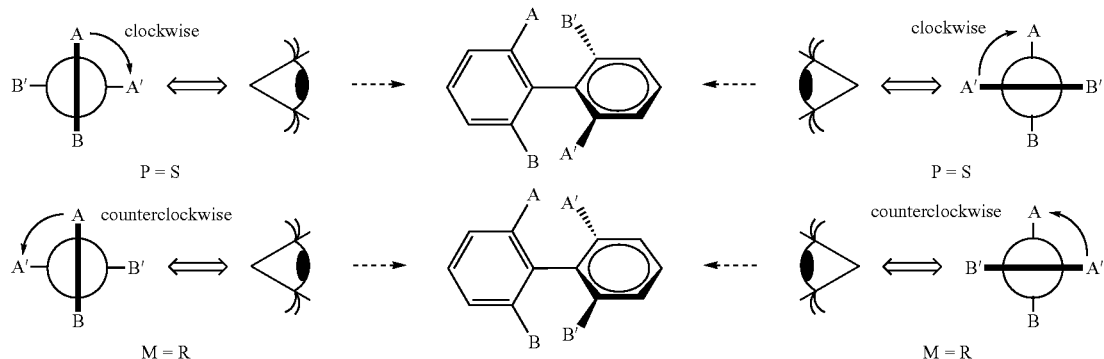

The research on the existence of axial chiral isomers of lesinurad was first reported in the Chinese patent application 201510086911.5 filed by the applicant, China Resources SECCO Pharmaceutical Co., Ltd. The application discloses that optically pure enantiomers were obtained via resolution by using instruments and equipments. Through experiments, it was determined that the front peak was the levorotary enantiomer (the optical rotation was −), and the rear peak was the dextrorotary enantiomer (the optical rotation was +). The relevant pharmacodynamic evaluation showed that the two single enantiomers had higher pharmaceutical activities than the racemate. Subsequently, the existence of axial chiral isomers of lesinurad was also reported in the Chinese patent applications 201510241034.4 and 201510918016.5. The literature, *ACS Med, chem. Lett.* 2017, 8, 299-303, reported that the levorotary isomer, i.e. (−)-lesinurad, was in R configuration, i.e. R-lesinurad, and the dextrorotary isomer, i.e. (+)-lesinurad was in S configuration, i.e. S-lesinurad.

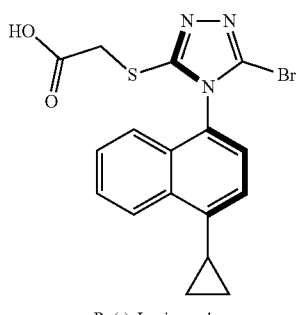

R-(-)-Lesinurad

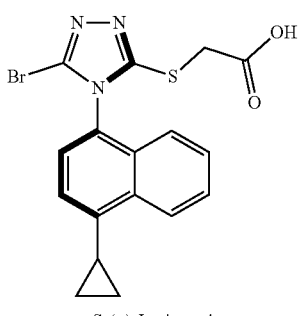

S-(+)-Lesinurad

Chinese patent application 201510086911.5 discloses that optically pure enantiomers were obtained via resolution by using instruments and equipments. For the current level of industrial production, the resolution method by using instruments is costly and cannot be industrialized. Chinese patent application 201610218702.6 discloses a resolution method of lesinurad enantiomers with an optically active amino alcohol derivative as resolving agent. However, the isomers obtained by the method have low optical purities and low total yields, the chiral resolving agents are expensive and the economic cost is high.

SUMMARY OF THE INVENTION

To solve the above-mentioned technical problem, the invention provides a resolution method of lesinurad racemate (i.e. 2-(5-bromo-4-(4-cyclopropylnaphthalen-1-yl)-4H-1,2,4-triazol-3-ylthio)acetic acid) to obtain optically pure R and S isomers of 2-(5-bromo-4-(4-cyclopropylnaphthalen-1-yl)-4H-1,2,4-triazol-3-ylthio)acetic acid.

The invention provides the following technical solutions:

A resolution method of axial chiral enantiomers of lesinurad, comprising:

(1) reacting axial chiral lesinurad racemate with resolving agent 1 in a solvent, and after filtration, subjecting the obtained solid to acid hydrolysis to give compound 1 after concentration;

(2) concentrating the mother liquor obtained by the filtration in step (1), and subjecting the obtained solid to acid hydrolysis to give compound 2 after concentration;

wherein, resolving agent 1 is quinine (CAS:130-95-0), quinidine (CAS:56-54-2), cinchonidine (CAS:485-71-2) or cinchonine (CAS:118-10-5).

According to the invention, the resolution method of axial chiral enantiomers of lesinurad, comprising:

(1) reacting axial chiral lesinurad racemate with resolving agent 1 in a solvent, cooling down the reaction solution to obtain a solid after filtration, and subjecting the obtained solid to acid hydrolysis to give compound 1 after concentration;

(2) concentrating the mother liquor obtained by the filtration in step (1), and subjecting the obtained solid to acid hydrolysis to give compound 2 after concentration;

wherein, resolving agent 1 is quinine (CAS:130-95-0), quinidine (CAS:56-54-2), cinchonidine (CAS:485-71-2) or cinchonine (CAS:118-10-5).

According to the invention, when resolving agent 1 is quinine or cinchonidine, the obtained compound 1 is lesinurad in R configuration, and compound 2 is lesinurad in S configuration.

When resolving agent 1 is cinchonine or quinidine, the obtained compound 1 is lesinurad in S configuration, and compound 2 is lesinurad in R configuration.

According to the invention, the solvent used in the reaction or acid hydrolysis in step (1) and that used in the acid hydrolysis in step (2) are the same or different, and are independently one, two or more selected from the group consisting of ester solvents, alcohol solvents, ketone solvents, ether solvents, and aromatic hydrocarbon solvents.

According to the invention, the pH values of the acid hydrolysis in step (1) and step (2) are the same or different, and are independently in the range of 1 to 4, preferably 2 to 3.

According to the invention, the molar ratio of the lesinurad racemate to resolving agent 1 in step (1) is (0.5-1.5):1, preferably 1:1.

According to the invention, in step (1), when resolving agent 1 is quinine or quinidine, the solvent used in the reaction is preferably an ester solvent or a ketone solvent, such as ethyl acetate or acetone.

According to the invention, in step (1), when resolving agent 1 is cinchonidine or cinchonine, the solvent used in the reaction is preferably an aromatic hydrocarbon solvent, such as toluene.

According to the invention, in step (1), the step of cooling down the reaction solution includes: cooling down the reaction system naturally, preferably to 10-30° C., keeping the system in an ice-water bath and stirring for 2-120 minutes, preferably 2-60 minutes, and more preferably 2-30 minutes.

According to the invention, the method further comprises the step of subjecting the obtained solid to one or more recrystallizations before the acid hydrolysis in step (1) and/or step (2).

According to the invention, the method further comprises step (3), and step (3) comprises: reacting compound 2 obtained in step (2) with resolving agent 2, cooling down the reaction solution to obtain a solid after filtration, and subjecting the obtained solid to acid hydrolysis to give compound 2 after concentration; wherein, resolving agent 2 is one selected from the group consisting of quinine, quinidine, cinchonidine and cinchonine.

Preferably, resolving agent 1 and resolving agent 2 in the invention are the same or different, more preferably different.

For example, when resolving agent 1 is quinine or cinchonidine, resolving agent 2 is cinchonine or quinidine; when resolving agent 1 is cinchonine or quinidine, resolving agent 2 is quinine or cinchonidine.

According to the invention, most preferably, resolving agent 1 is quinine, and resolving agent 2 is cinchonine; or resolving agent 1 is cinchonine, and resolving agent 2 is quinine.

According to the invention, the method further comprises step (4), and step (4) comprises: adjusting the pH of the aqueous phase obtained after the acid hydrolysis in step (1) and/or step (2) to 9-11, preferably 10, to obtain a solid after filtration, and recovering resolving agent 1.

According to the invention, when the method comprises step (3), it further comprises step (5); and step (5) comprises: adjusting the pH of the aqueous phase obtained after the acid hydrolysis in step (3) to 9-11, preferably 10, to obtain a solid after filtration, and recovering resolving agent 2.

The invention further provides use of a resolving agent in the resolution of lesinurad racemate, wherein the resolving agent is selected from the group consisting of quinine, quinidine, cinchonidine and cinchonine.

Beneficial Effects

The method of the invention uses optically pure quinoline natural products and derivatives thereof as chemical resolving agents to chemically resolve lesinurad racemate. The axial chiral enantiomer of lesinurad in R configuration can be obtained with a chiral purity ee of up to 100% and a total yield of 90% or more. The axial chiral enantiomer of lesinurad in S configuration can be obtained with a chiral purity ee of up to 99.9% and a total yield of 80% or more. Furthermore, the chiral resolving agents used are cheap and easy to obtain, can be conveniently recovered and reused, thus reducing the separation cost and facilitating industrial production.

For example, when quinine or cinchonine is used for resolution, the method of the invention has multiple advantages compared with the prior art, and the details are shown below:

salts and the solvent was mixed in a colloidal state, which was difficult to operate and filter during the filtration process, not beneficial to industrial production. However, by using the resolving agents of the invention, after the salt formation of the resolving agents with lesinurad, the solid was precipitated in a good crystalline state and in the form of powder, which could be separated from the solvent by simple filtration. Compared with the colloidal substances obtained after the precipitation of the salts formed by the reaction of amino alcohol resolving agents with lesinurad, the products of the invention obtained after the salt formation process are easy to separate and thus is beneficial to industrial production.

Definition and Description of Terms

The ester solvents used in the invention include but are not limited to ethyl acetate, methyl acetate, isopropyl acetate, butyl acetate, isoamyl acetate, and diethyl malonate.

The alcohol solvents used in the invention include but are not limited to methanol, ethanol, propanol, isopropanol, butanol, pentanol, decanol, n-dodecanol, cyclopentanol, cyclohexanol, benzyl alcohol and phenylethanol.

The ketone solvents used in the invention include but are not limited to acetone, 1-butanone and cyclohexanone.

The ether solvents used in the invention include but are not limited to ethyl ether, methyl ethyl ether, dipropyl ether, dibutyl ether, 1,4-dioxane, furan and methylfuran.

The ether solvents used in the invention include but are not limited to toluene and chlorobenzene.

In an embodiment of the invention, where the reaction temperature or operating temperature is not specified, it usually refers to room temperature (10-30° C., such as 20-25° C.).

| | Prior art | | | The invention | |
|---|---|---|---|---|---|
| Resolution of R isomer | Optical purity (ee) | 99.9% | Resolution of R isomer | Optical purity (ee) | 100% |
| | Total yield | 40% | | Total yield | 90.8% |
| | Resolving agent used | (1R,2S)-(−)-2-amino-1,2-diphenylethanol | | Resolving agent used | quinine |
| | Price of resolving agent (RMB/kg, quoted on MOLBASE's website) | 6263.00 | | Price of resolving agent (RMB/kg, quoted on MOLBASE's website) | 2701.00 |
| | Recovery of resolving agents | non-recoverable | | Recovery of resolving agents | recoverable |
| | Optical purity (ee) of S isomer obtained from mother liquor after concentration | 24.4% | | Optical purity (ee) of S isomers obtained from mother liquor after concentration | 94.5% |
| Resolution of S isomer | Optical purity | 99.9% | Resolution of S isomer | Optical purity | 99.9% |
| | Total yield | 39% | | Total yield | 82.8% |
| | Resolving agent used | (1S,2R)-2-amino-1,2-diphenylethanol | | Resolving agent used | cinchonine |
| | Price of resolving agent (RMB/kg, quoted on MOLBASE's website) | 5786.00 | | Price of resolving agent (RMB/kg, quoted on MOLBASE's website) | 2346.00 |
| | Optical purity (ee) of R isomer obtained from mother liquor after concentration | unknown | | Optical purity (ee) of R isomers obtained from mother liquor after concentration | 40% |

When quinine is replaced with cinchonidine or cinchonine is replaced with quinidine, the same resolution effect as that of quinine or cinchonine in the above table can be achieved.

The inventors found that in the method of the invention, after the salts had been formed by the reaction of lesinurad with the resolving agent, during the cooling and precipitation stage, when the reaction system was cooled down naturally and then kept in a nice-water bath and stirred for a period of time, the salt precipitated well, and the two enantiomers were separated with relatively high optical rotation after acid dissociation.

Moreover, the inventor found that during the processes of salt formation and crystallization of the amino alcohol resolving agents with lesinurad, the obtained intermediate In an embodiment of the invention, the ratios of the mixed solvents are all volume ratios.

In the invention, ee refers to enantiomeric excess, which represents the excess of one enantiomer over the other, usually expressed as a percentage. Enantiomeric excess (ee) is used for evaluating the optical purity of a chiral compound. The higher the ee is, the higher the optical purity is. The ee of a pure chiral compound is 100%.

As shown below, according to the analysis method of axial enantiomers, Formula 3 is the enantiomer in R configuration.

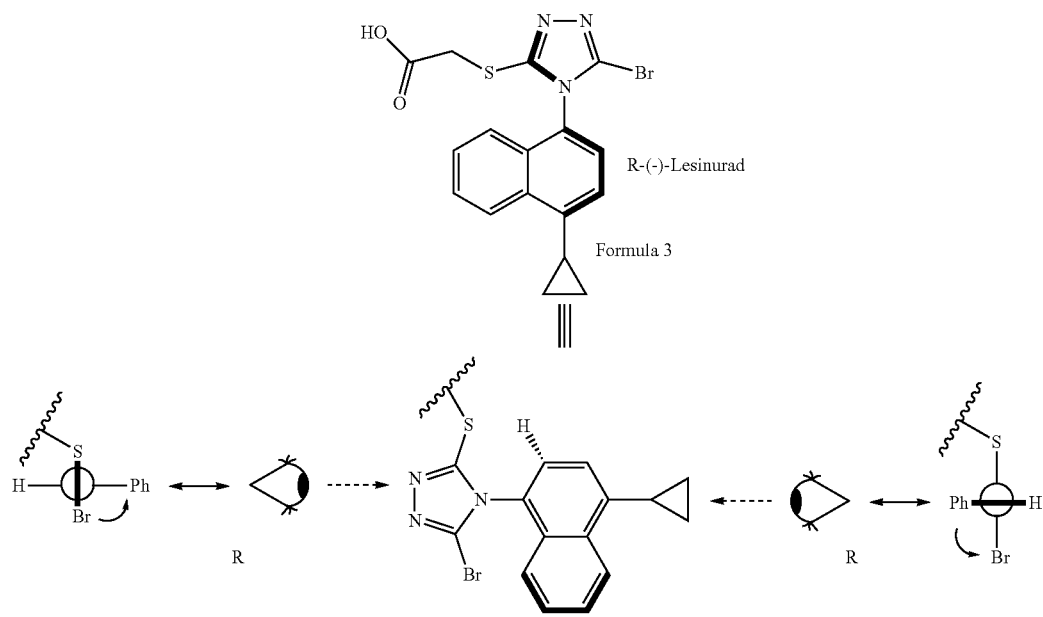

R-(-)-Lesinurad

Formula 3

As shown below, according to the analysis method of axial enantiomers, Formula 4 is the enantiomer in S configuration.

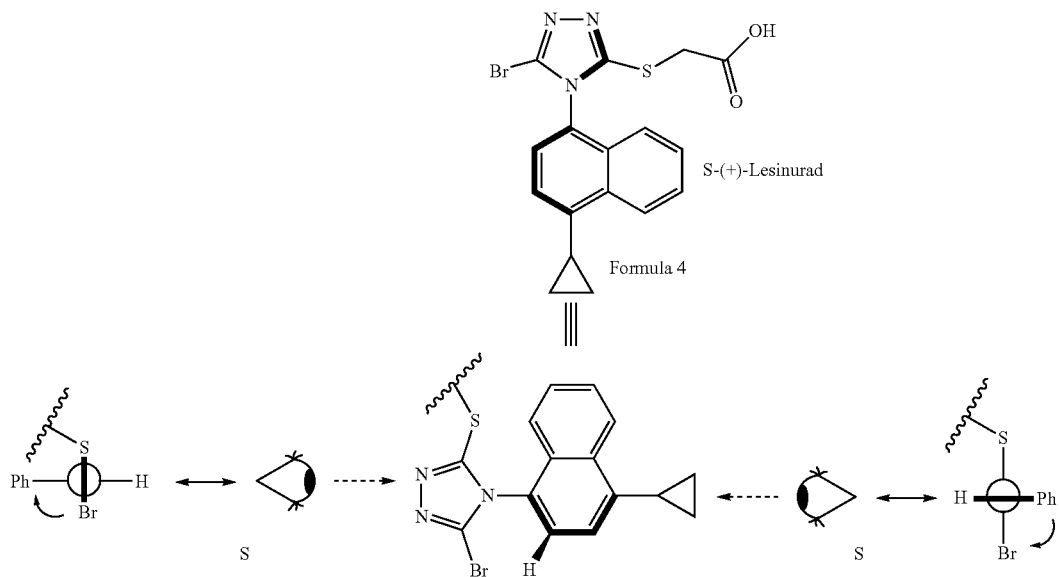

S-(+)-Lesinurad

Formula 4

In the invention, the terms "axial chiral enantiomer", "enantiomer", and "axial chiral isomer" have the same meaning. It should be understood by those skilled in the art that lesinurad of the prior art is a racemate in (R,S)-configuration. In the invention, for the sake of brevity, racemic lesinurad is sometimes referred to as "lesinurad racemate" or "racemate lesinurad".

Correspondingly, the terms "R (configuration) axial chiral enantiomer", "R (configuration) enantiomer", "R (configuration) axial chiral isomer" and "R-lesinurad" have the same meaning, and all refer to the compound represented by Formula 3.

Similarly, the terms "S (configuration) axial chiral enantiomer", "S (configuration) enantiomer", "S (configuration) axial chiral isomer" and "S-lesinurad" have the same meaning, and all refer to the compound represented by Formula 4.

In an embodiment, the organic solvent used for the recrystallization may be determined through experiments.

EXAMPLES

Figure 1:
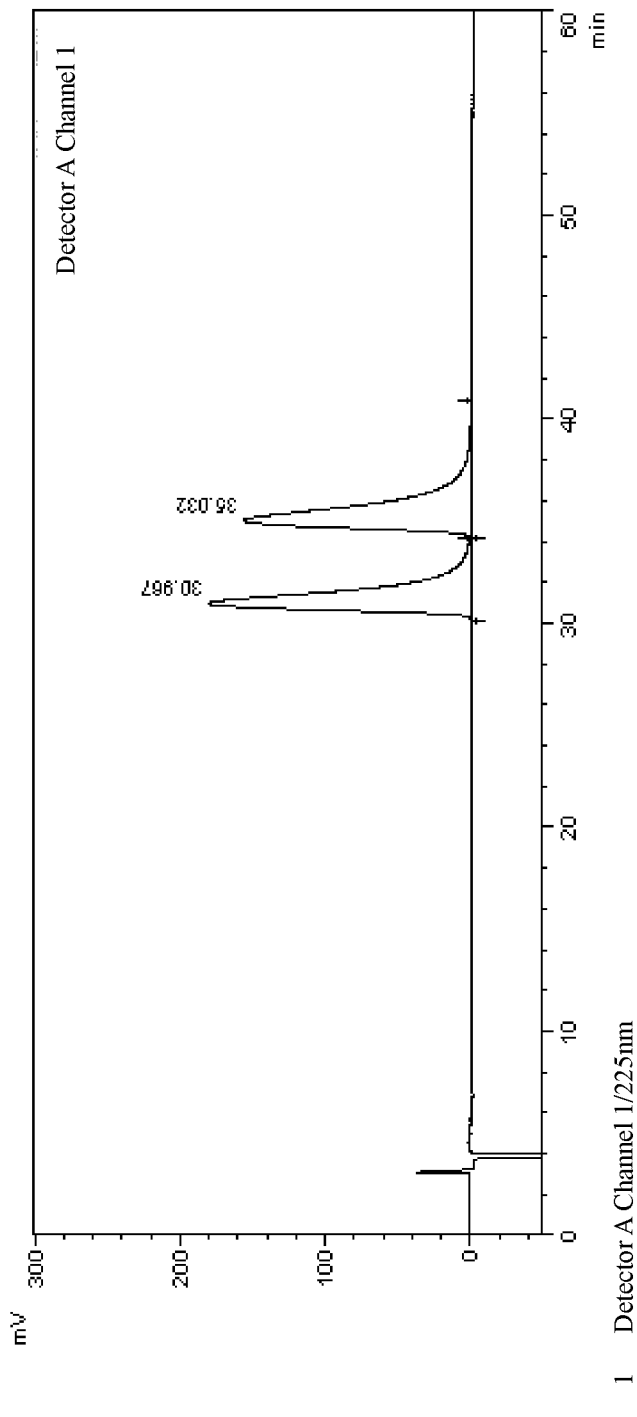
FIG. 1 is an HPLC chromatogram of the lesinurad racemate.

Hereinafter, the invention is further described in detail with reference to the specific examples. The following examples are intended to give an exemplary description and explanation of the invention, rather than limit the protection scope of the invention. All realizable technical solutions based on the above contents of the invention are deemed to fall within the protection scope of the invention.

The invention involves the addition amounts, contents and concentrations of various substances, and the percentages mentioned herein all refer to percentages by mass, unless otherwise specified.

Experimental Reagents and Detection Methods

1. Reagents

Reagents: the organic solvents, acidifying agents and alkalinizing agents, etc., used in the examples of the invention, are all commercially available and of analytical grade, unless otherwise noted, and can be used directly.

2. Detection Methods

Polarimeter: Automatic Polarimeter P850

Mass spectrometer: Agilent 6120 Quadrupole LC/MS Mass Spectrometer (ES-API source, positive ion mode)

The chromatographic conditions for chiral detection:

Column: Chrialpak AD-H, 4.6×250 mm, 5 μm

Mobile phase: n-hexane:anhydrous ethanol:diethylamine=90:10:0.2 Detection wavelength: 225 nm Column temperature: 30° C.

Injection volume: 10 μl

Flow rate: 1.0 ml/min.

Example 1

Racemic lesinurad (2-(5-bromo-4-(4-cyclopropylnaphthalen-1-yl)-4H-1,2,4-triazol-3-ylthio)acetic acid) was synthesized according to the method described in patent documents WO2009070740A2, CN103524440A or WO2014008295A1. The specific synthetic route is as follows:

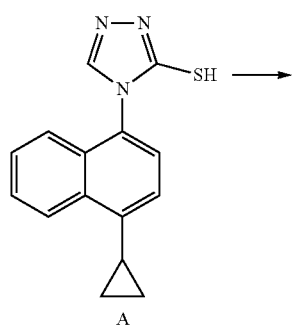

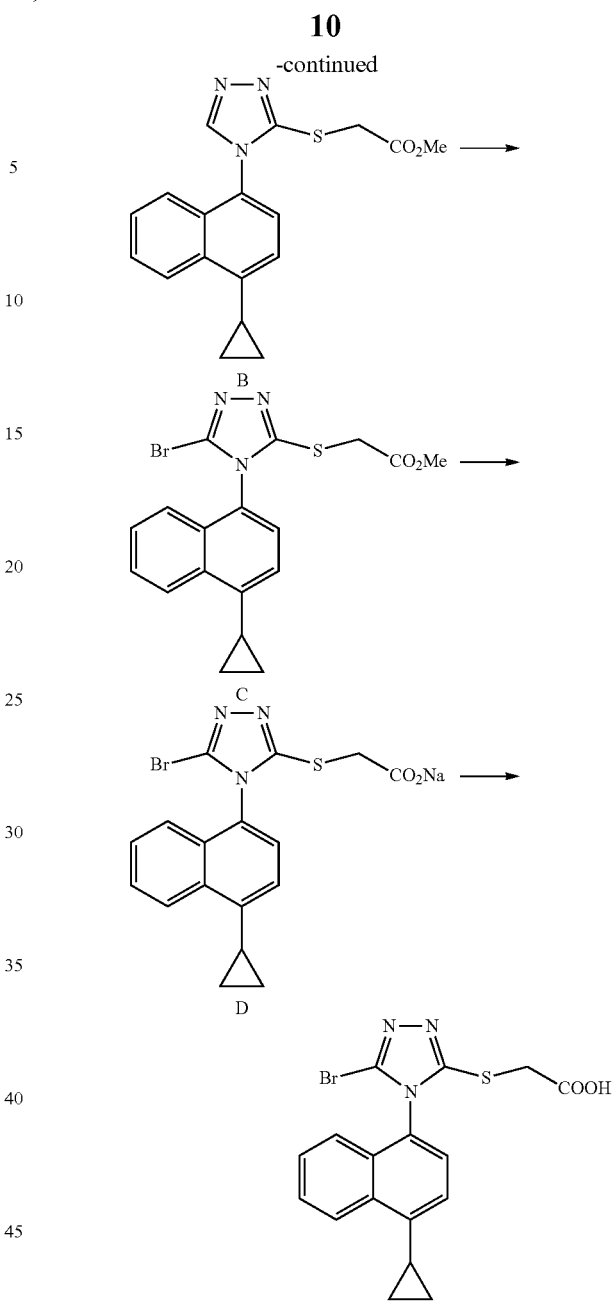

4-(1-cyclopropylnaphthalen-4-yl)-4H-1,2,4-triazol-thiol (compound A, 14.5 g, 54.2 mmol) was dissolved in 150 ml DMF, potassium carbonate (11.2 g, 81.3 mmol) was added to the solution, and then methyl bromoacetate (5.88 g, 54.2 mmol) was added dropwise. After the addition was complete, the solution was raised to 50° C. and kept for 4 hours. After the reaction was complete, the reaction solution was partitioned between water (100 ml) and ethyl acetate (100 ml). The aqueous phase was extracted with ethyl acetate (2×100 ml). The organic phases were combined, washed with saline (6×150 ml), dried over anhydrous sodium sulfate for 1 h, and filtrated with suction. The filtrate was evaporated to dryness to obtain 15.6 g white-like powder, which was intermediate B, with a yield of 85%. LC-MS (m/z): $[M+H]^+$=340.1.

Intermediate B (46.0 g, 135.7 mmol) was dissolved in THF (300 ml) at 35-42° C. and stirred until clear. The solution was cooled down to 27-32° C., NBS (33.764 g, 189.7 mmol) was added, and the reaction solution was kept at the constant temperature for 30 mins (as the reaction was exothermic and the temperature would rise slowly, the temperature should be properly controlled). The reaction was monitored by TLC (PE:EA=1:1). After the reaction was complete, the reaction solution was cooled down to 2-7° C. While maintaining at that temperature, toluene (460 ml) was added to the solution, and then purified water (460 ml) was added dropwise (as the process was exothermic, water should be added slowly). The solution was stirred for 10 mins and then let stand. The system separated into layers. The aqueous phase was removed off. The organic phase was washed with sodium metabisulfite solution until the aqueous phase was colorless or of light-color (the temperature was kept at 2-7° C. during the washing process). The organic phase was heated to 18-25° C., and washed with water (230 ml) and then sodium bicarbonate solution until pH>8. The organic phase was a solution of intermediate C in toluene, which was directly used in the next step. LC-MS (m/z): [M+H]$^+$=420.0.

At 10-15° C., to the organic phase of intermediate C, a sodium hydroxide solution (230 ml) was added and then stirred for 2-3 h. The organic phase was monitored by TLC (PE:EA=1:1). After the reaction was complete, the solution was partitioned, the organic phase was washed with water (100 ml) and the aqueous phases were combined. Ethyl acetate (100 ml) was added to the aqueous phase and the organic phase was discarded. At 40° C., the aqueous phase was evaporated under reduced pressure until no distillate was evaporated out. The aqueous phase was cooled down to 0-5° C. and stirred for 2 h, and a white solid was precipitated. After suction filtration, the filter cake was washed with purified water, and dried under vacuum at 40-45° C. for 30 h to obtain intermediate D. Intermediate D was dissolved in water. HBr (2 M) was added dropwise to the solution, the pH of the system was adjusted to 4-5, and a white solid was precipitated. After suction filtration and drying, 41.7 g white solid was obtained, which was lesinurad, with a yield of 76%. LC-MS (m/z): [M+H]$^+$=404.0. (Specific rotation [a]$^{20}_D$=0, C=1, CH$_3$OH). It was detected by high-performance liquid chromatography (HPLC, with the result shown in FIG. 1.

Example 2

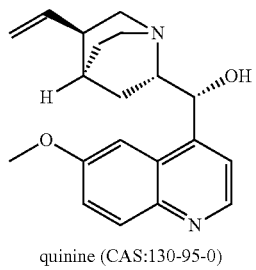 [SMILES: C=C[C@H]1CN2CC[C@H]1C[C@H]2[C@H](O)c1ccnc2ccc(OC)cc12]

quinine (CAS:130-95-0)

Salt formation: 10 g of lesinurad racemate (1.0 eq.) was added to ethyl acetate (100 ml). The mixture was heated to 70° C., and quinine (8.1 g, 1.0 eq.) was slowly added under stirring. The mixture was heated to reflux, and kept at the constant temperature for 1 h. The reaction system was slowly and naturally cooled down to room temperature, then kept in an ice-water bath and stirred for 30 mins. After filtration, the filter cake was washed with ethyl acetate (20 ml) to obtain 9.1 g white solid powder A (salt of lesinurad in R configuration), ee=97.9%. The filtrate was concentrated by rotary evaporation and dried to obtain 9.0 g white solid powder C (salt of lesinurad in S configuration), ee=94.5%.

Figure 2:
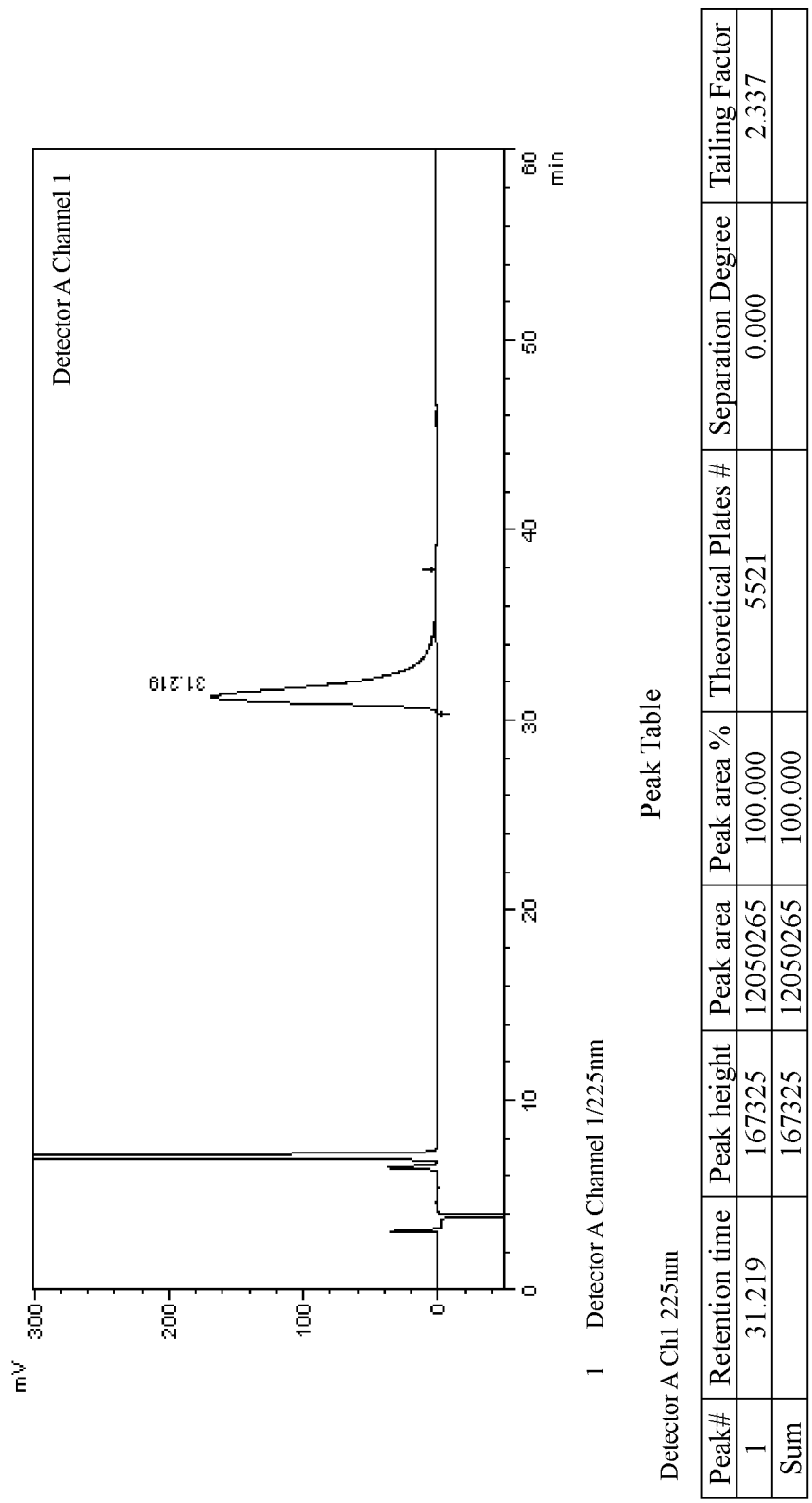
FIG. 2 is an HPLC chromatogram of the intermediate salt of the R chiral enantiomer of lesinurad.

Recrystallization: 9.1 g of the above white solid powder A was added to ethyl acetate (90 ml) under stirring. The mixture was heated to reflux, and kept at the constant temperature for 1 h. The reaction system was slowly and naturally cooled down to room temperature, then kept in an ice-water bath and stirred at the constant temperature for 30 mins. After filtration, the filter cake was washed with ethyl acetate (20 ml) to obtain 8.5 g white solid powder B (salt of lesinurad in R configuration), ee=100%. It was detected by high-performance liquid chromatography (HPLC), with the result shown in FIG. 2, and the retention time t was 31.219 min.

Figure 3:
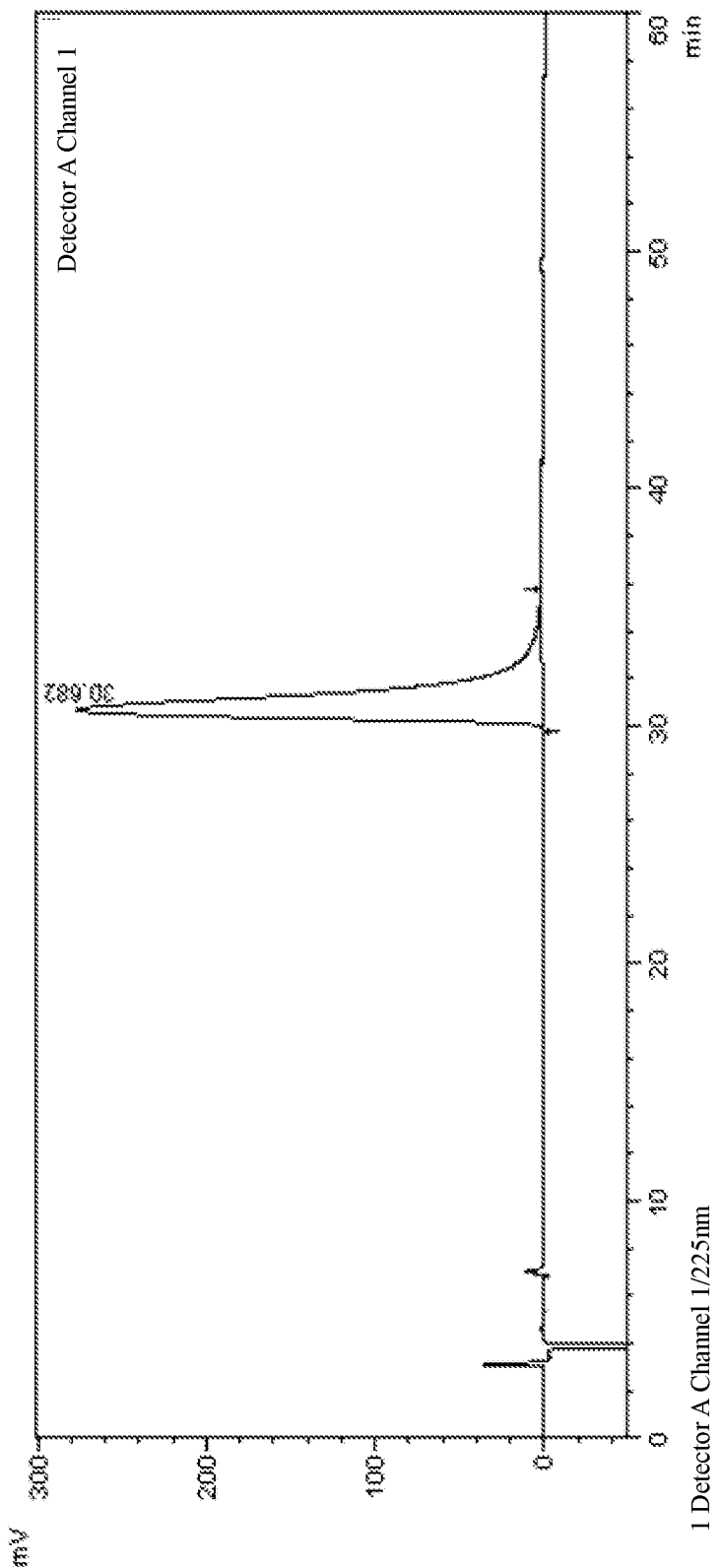
FIG. 3 is an HPLC chromatogram of the R chiral enantiomer of lesinurad.

Acid dissociation: 8.5 g of the above white solid powder B was dissolved in dichloromethane (85 ml), and then H$_2$O (85 ml) was added. To the mixture, diluted hydrochloric acid (2 mol/L) was added dropwise under stirring to adjust the pH to 2-3. The mixture was further stirred at room temperature for 15 mins, and then separated into phases. The obtained aqueous phase was recovered for use. The organic phase was washed with water/diluted hydrochloric acid (2 mol/L) (20 ml/0.5 ml), then washed with water (20 ml), dried over anhydrous sodium sulfate, and filtered. The filtrate was concentrated, and dried to obtain 4.54 g white solid, i.e. (R)-2-(5-bromo-4-(4-cyclopropylnaphthalen-1-yl)-4H-1,2,4-triazol-3-ylthio)acetic acid (specific rotation [a]$^{20}_D$=−9.0°−−12.5°, C=1, CH$_3$OH), ee=100%. It was detected by high-performance liquid chromatography (HPLC), with the result shown in FIG. 3. The retention time t was 30.682 min, and the total yield was 90.8%. ESI(M+H)=404.

The recovered aqueous phase after the above acid dissociation was added into a 500 ml reaction flask, and a NaOH solution (2 mol/L) was dropwise added under stirring at 0° C. to adjust the pH to 10. The system turned into a white cloudy mixture. The mixture was further stirred at room temperature for 15 mins, filtered, and dried to obtain 3.5 g white solid quinine. ESI(M+H)=325.

Example 3

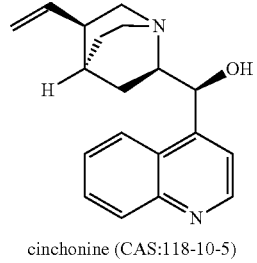 [SMILES: C=C[C@H]1CN2CC[C@H]1C[C@@H]2[C@@H](O)c1ccnc2ccccc12]

cinchonine (CAS:118-10-5)

Salt formation: 10 g of lesinurad racemate (1.0 eq.) was added to toluene (100 ml). The mixture was heated to 105° C., and cinchonine (7.3 g, 1.0 eq.) was slowly added under stirring. The mixture was heated to reflux, and kept at the constant temperature for 1 h. The reaction system was slowly and naturally cooled down to room temperature, then kept in an ice-water bath and stirred for 30 mins.

After filtration, the filter cake was washed with toluene (20 ml) to obtain 8.9 g white-like solid (salt of lesinurad in S configuration, a crude product), ee=80%. The filtrate was concentrated by rotary evaporation and dried to obtain 9.1 g white solid powder (salt of lesinurad in R configuration, a crude product), ee=40%.

Figure 4:
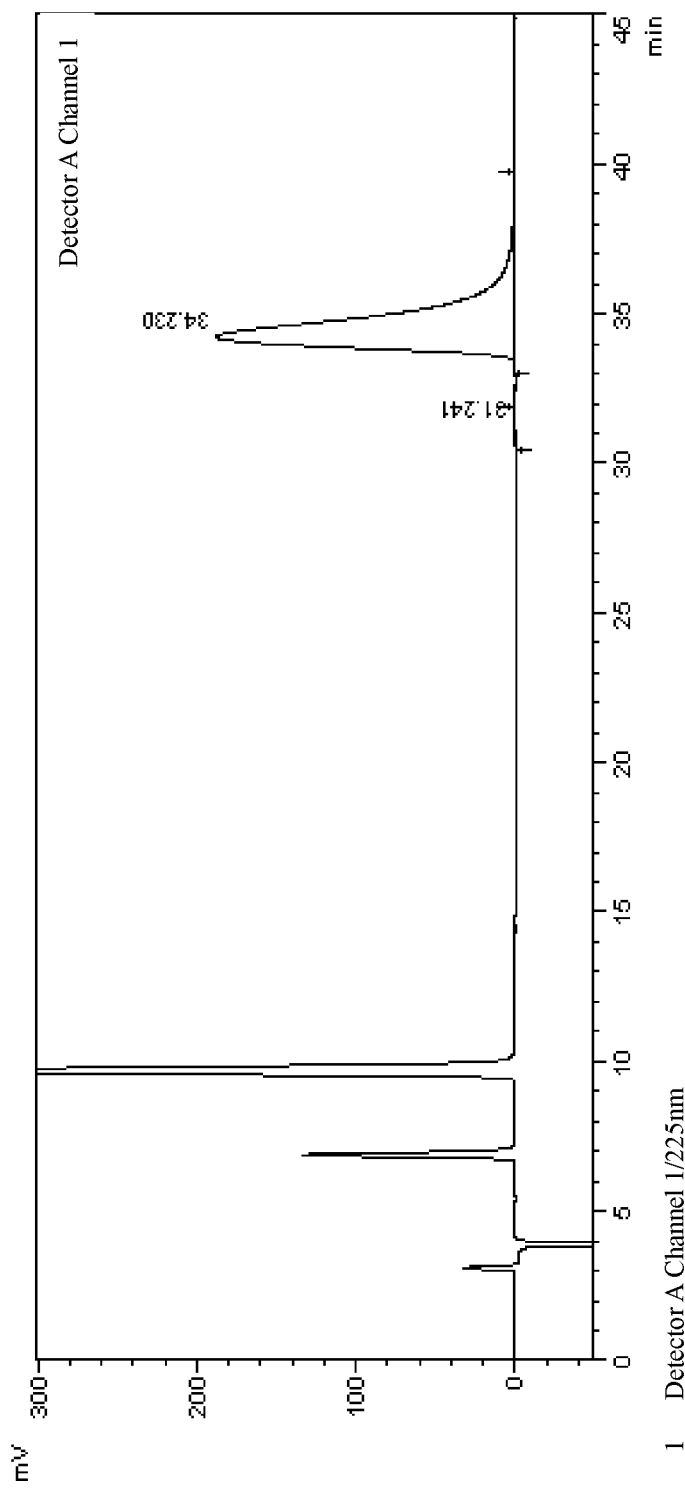
FIG. 4 is an HPLC chromatogram of the intermediate salt of the S chiral enantiomer of lesinurad.

Recrystallization: 8.9 g of the above white-like solid (salt of lesinurad in S configuration, a crude product) was added to toluene (90 ml) under stirring. The mixture was heated to reflux, and then kept at the constant temperature for 1 h. The reaction system was slowly and naturally cooled down to room temperature, then kept in an ice-water bath and stirred for 30 mins. After filtration, the filter cake was washed with toluene (20 ml) to obtain 5.5 g white solid (salt of lesinurad in S configuration), ee=99.9%. It was detected by high-performance liquid chromatography (HPLC), with the result shown in FIG. 4, and the retention time t was 34.230 min.

Figure 5:
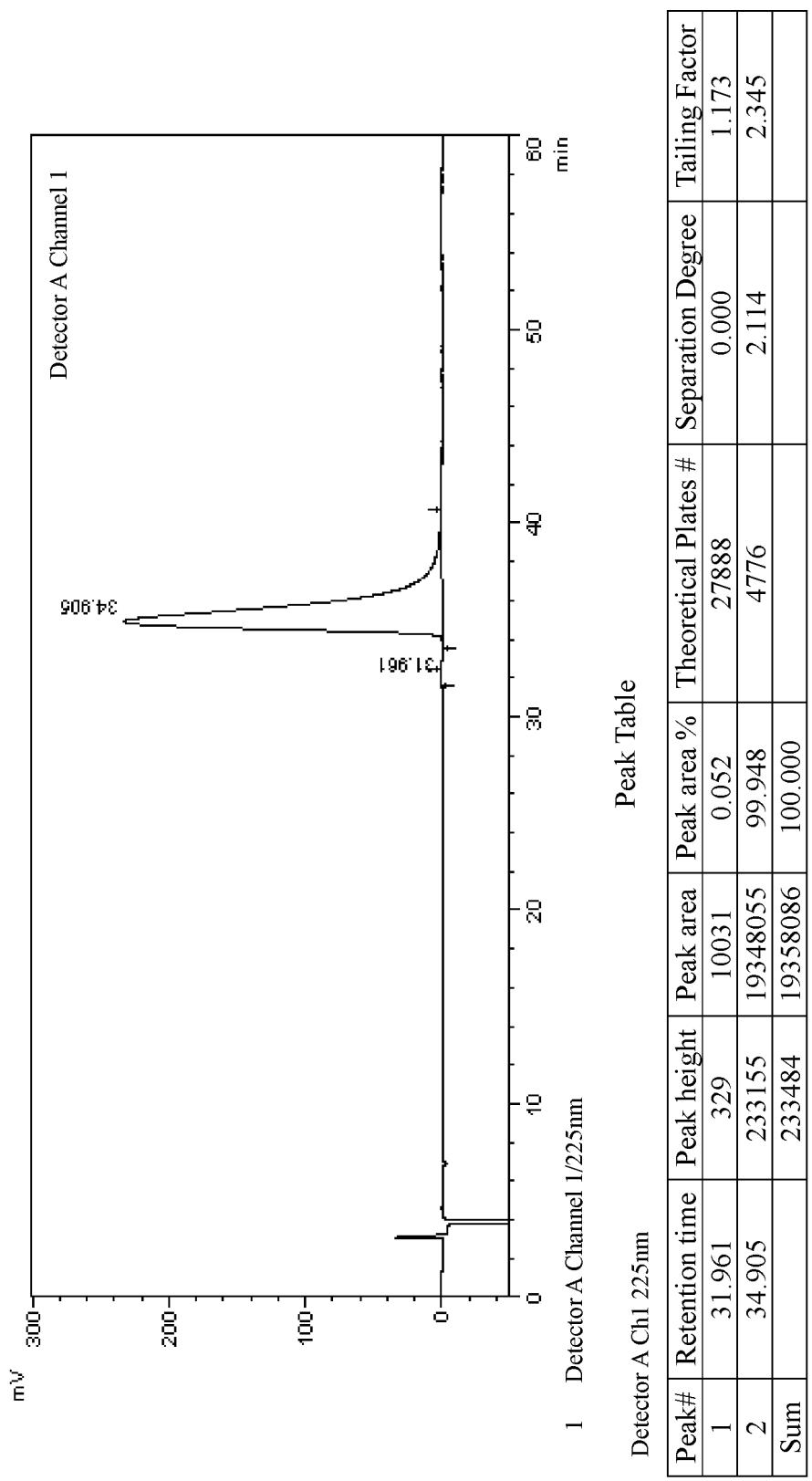
FIG. 5 is an HPLC chromatogram of the S chiral enantiomer of lesinurad.

Acid dissociation: 5.5 g of the above white solid was dissolved in dichloromethane (60 ml), and $H_2O$ (60 ml) was added. To the mixture, diluted hydrochloric acid (2 mol/L) was added dropwise under stirring to adjust the pH to 2-3. The solution was further stirred at room temperature for 15 mins, and then separated into phases. The obtained aqueous phase was recovered for use. The organic phase was washed with water/diluted hydrochloric acid (2 mol/l) (15 ml/0.4 ml), then washed with water (15 ml), dried over anhydrous sodium sulfate, and filtered. The filtrate was concentrated, and dried to obtain 3.1 g white solid, i.e. (S)-2-(5-bromo-4-(4-cyclopropylnaphthalen-1-yl)-4H-1,2,4-triazol-3-ylthio)acetic acid, ee=99.9% (specific rotation $[a]^{20}_D$=+9.5°-+12.5°, C=1, $CH_3OH$). It was detected by high-performance liquid chromatography (HPLC), with the result shown in FIG. 5, the retention time t was 34.905 min, and the total yield was 62.0%. ESI(M+H)=404.

Example 4

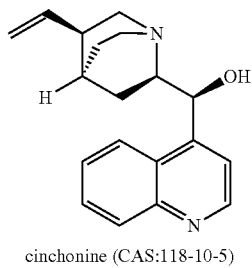 [SMILES: C=C[C@H]1CN2CC[C@H]1C[C@@H]2[C@@H](O)c1ccnc2ccccc12]

cinchonine (CAS:118-10-5)

Acid dissociation: 9.0 g of the obtained white solid powder C (salt of lesinurad in S configuration) in Example 2 was dissolved in dichloromethane (90 ml), and $H_2O$ (90 ml) was added. To the mixture, diluted hydrochloric acid (2 mol/l) was added dropwise under stirring to adjust the pH to 2-3. The solution was further stirred at room temperature for 15 mins, and then separated into phases. The obtained aqueous phase was recovered for use. The organic phase was washed with water/diluted hydrochloric acid (2 mol/l) (20 ml/0.5 ml), then washed with water (20 ml), dried over anhydrous sodium sulfate, and filtered. The filtrate was concentrated, and dried to obtain 4.75 g white solid, i.e. (S)-2-(5-bromo-4-(4-cyclopropylnaphthalen-1-yl)-4H-1,2, 4-triazol-3-ylthio)acetic acid (a crude product). ESI-(M+H)=404.

Salt formation: 4.75 g of the above white solid was added to toluene (50 ml). The mixture was heated to 105° C., and cinchonine (3.5 g, 1.0 eq.) was slowly added under stirring. The mixture was heated to reflux, and kept at the constant temperature for 1 h. The reaction system was slowly and naturally cooled down to room temperature, then kept in an ice-water bath and stirred for 30 mins. After filtration, the filter cake was washed with toluene (20 ml) to obtain 7.8 g white-like solid (salt of lesinurad in S configuration), ee=98.7%.

Recrystallization: 7.8 g of the above white-like solid (salt of lesinurad in S configuration) was added to toluene (90 ml) under stirring. The mixture was heated to reflux, and kept at the constant temperature for 1 h. The reaction system was slowly and naturally cooled down to room temperature, then kept in an ice-water bath and stirred at the constant temperature for 30 mins. After filtration, the filter cake was washed with toluene (20 ml) to obtain 7.3 g white solid (salt of lesinurad in S configuration), ee=99.9%.

Acid dissociation: 6.9 g of the above white solid was dissolved in dichloromethane (70 ml), and $H_2O$ (70 ml) was added. To the mixture, diluted hydrochloric acid (2 mol/l) was added dropwise under stirring to adjust the pH to 2-3. The solution was further stirred at room temperature for 15 mins, and then separated into phases. The obtained aqueous phase was recovered for use. The organic phase was washed with water/diluted hydrochloric acid (2 mol/l) (15 ml/0.4 ml), then washed with water (15 ml), dried over anhydrous sodium sulfate, and filtered. The filtrate was concentrated, and dried to obtain 4.2 g white solid, i.e. (S)-2-(5-bromo-4-(4-cyclopropylnaphthalen-1-yl)-4H-1,2,4-triazole-3-yl-thio)acetic acid, ee=99.9%, with a total yield of 82.8%. ESI(M+H)=404.

The above illustrates the exemplary embodiments of the invention. However, the embodiments are not intended to limit the protection scope of the invention. Any modification, equivalent alternative, and improvement made without departing from the spirit and principle of the invention should fall within the protection scope of the invention.

The invention claimed is:

1. A resolution method of axial chiral enantiomers of lesinurad, comprising:
   (1) reacting axial chiral lesinurad racemate with a first resolving agent in a first solvent to form a first reaction solution, filtering the first reaction solution to obtain a first solid and a mother liquor, and subjecting the first solid to acid hydrolysis in a second solvent to obtain a first compound; and
   (2) concentrating the mother liquor obtained in step (1) to obtain a second solid, and subjecting the second solid to acid hydrolysis in a third solvent to obtain a second compound,
   wherein the first resolving agent is quinine (CAS:130-95-0), quinidine (CAS:56-54-2), cinchonidine (CAS:485-71-2), or cinchonine (CAS:118-10-5), and
   wherein the first compound comprises more R-(−)-lesinurad than S-(+)-lesinurad and the second compound comprises more S-(+)-lesinurad than R-(−)-lesinurad, or
   wherein the first compound comprises more S-(+)-lesinurad than R-(−)-lesinurad and the second compound comprises R-(−)-lesinurad than S-(+)-lesinurad.

2. The method according to claim 1, wherein the first solvent, the second solvent, the third solvent are the same or different, and are independently selected from ester solvents, alcohol solvents, ketone solvents, ether solvents, aromatic hydrocarbon solvents, and mixtures thereof.

3. The method according to claim 1, wherein the acid hydrolysis in step (1) and the acid hydrolysis in step (2) are conducted at a same or different pH value independently ranging from 1 to 4.

4. The method according to claim 1, wherein the molar ratio of lesinurad racemate to the first resolving agent in step (1) is (0.5-1.5):1.

5. The method according to claim 1, wherein, in step (1), when the first resolving agent is quinine or quinidine, the first solvent is an ester solvent or a ketone solvent; and
in step (1), when the first resolving agent is cinchonidine or cinchonine, the first solvent is an aromatic hydrocarbon solvent.

6. The method according to claim 1, further comprising cooling down the first reaction solution to a temperature of 10-30° C., or in an ice-water bath under stirring for 2-120 minutes.

7. The method according to claim 1, wherein, the method further comprises subjecting the first solid to one or more recrystallizations before the acid hydrolysis in step (1) and/or subjecting the second solid to one or more recrystallizations before the acid hydrolysis in step (2).

8. The method according to claim 1, further comprising step (3): reacting the second compound with a second resolving agent to form a second reaction solution, cooling down the second reaction solution, filtering the second reaction solution to obtain a third solid, and subjecting the third solid to acid hydrolysis, wherein the second resolving agent 2 is quinine, quinidine, cinchonidine, or cinchonine.

9. The method according to claim 1, further comprising recovering the first resolving agent by: separating the reaction solution from the acid hydrolysis in step (1) or in step (2) to obtain an aqueous phase; adjusting a pH value of the aqueous phase to 9-11; and precipitating and filtering the first resolving agent from the aqueous phase.

10. The method according to claim 8, further comprising recovering the second resolving agent by: separating the reaction solution from the acid hydrolysis in step (3) to obtain an aqueous phase; adjusting a pH value of the aqueous phase to 9-11; and precipitating and filtering the second resolving agent from the aqueous phase.

* * * * *